(12) United States Patent
Ikeda et al.

(10) Patent No.: US 11,653,822 B2
(45) Date of Patent: May 23, 2023

(54) ENDOSCOPE

(71) Applicant: FUJIFILM Corporation, Tokyo (JP)

(72) Inventors: Toshiyuki Ikeda, Kanagawa (JP); Yuji Shihota, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 460 days.

(21) Appl. No.: 16/813,696

(22) Filed: Mar. 9, 2020

(65) Prior Publication Data

US 2020/0297189 A1 Sep. 24, 2020

(30) Foreign Application Priority Data

Mar. 20, 2019 (JP) .............................. JP2019-052438

(51) Int. Cl.
*A61B 1/005* (2006.01)
*A61B 1/00* (2006.01)
*A61B 1/01* (2006.01)

(52) U.S. Cl.
CPC ........ *A61B 1/0057* (2013.01); *A61B 1/00006* (2013.01); *A61B 1/0053* (2013.01); *A61B 1/01* (2013.01)

(58) Field of Classification Search
CPC . A61B 1/0057; A61B 1/00006; A61B 1/0053; A61B 1/01
See application file for complete search history.

(56) References Cited

U.S. PATENT DOCUMENTS

| | | | |
|---|---|---|---|
| 10,172,600 B2 | 1/2019 | Okamoto et al. | |
| 10,792,116 B2 | 10/2020 | Haraguchi et al. | |
| 2014/0031626 A1 | 1/2014 | Schwarz | |
| 2014/0251042 A1* | 9/2014 | Asselin | F16H 21/40 74/89 |
| 2014/0309625 A1* | 10/2014 | Okamoto | A61B 34/71 606/1 |

(Continued)

FOREIGN PATENT DOCUMENTS

| | | |
|---|---|---|
| JP | H04197235 | 7/1992 |
| JP | 2014223293 | 12/2014 |

(Continued)

OTHER PUBLICATIONS

"Office Action of Japan Counterpart Application" with English translation thereof, dated Oct. 5, 2021, p. 1-p. 5.

*Primary Examiner* — Anh Tuan T Nguyen
*Assistant Examiner* — Rynae E Boler
(74) *Attorney, Agent, or Firm* — JCIPRNET (57) ABSTRACT

Provided is an endoscope capable of operating a bending part with a higher degree of freedom while enabling a related-art operation of moving a pair of bending operating wires forward and backward. The endoscope has an insertion part having a bendable bending part; an operating part continuously provided on a proximal end side of the insertion part; a pair of bending operating wires inserted into the insertion part and fixed to a distal end side of the insertion part; a first bending operating mechanism that operates the bending part by moving the pair of bending operating wires forward and backward in conjunction with each other; and a second bending operating mechanism that operates the bending part by independently moving the pair of bending operating wires forward and backward.

11 Claims, 9 Drawing Sheets

(56) References Cited

U.S. PATENT DOCUMENTS

| | | | |
|---|---|---|---|
| 2014/0371534 A1* | 12/2014 | Okamoto | A61B 1/0057 600/118 |
| 2016/0073856 A1* | 3/2016 | Saito | A61B 1/0057 600/149 |
| 2020/0390508 A1 | 12/2020 | Haraguchi et al. | |
| 2021/0105385 A1* | 4/2021 | Uchida | A61B 1/0016 |

FOREIGN PATENT DOCUMENTS

| | | |
|---|---|---|
| JP | 2018114231 | 7/2018 |
| WO | 2013108776 | 7/2013 |
| WO | 2016136628 | 9/2016 |
| WO | 2016190273 | 12/2016 |

\* cited by examiner

ENDOSCOPE

CROSS-REFERENCE TO RELATED APPLICATION

This application claims priority under 35 USC 119 from Japanese Patent Application No. 2019-052438 filed on Mar. 20, 2019, the disclosure of which is incorporated by reference herein in its entirety.

BACKGROUND OF THE INVENTION

1. Field of the Invention

The present disclosure relates to an endoscope.

2. Description of the Related Art

For example, in the medical field, an endoscope to be inserted into the body of a subject, such as a patient, is known. Generally, endoscopes include an insertion part having a bendable bending part, and an operating part continuously provided on a proximal end side of the insertion part, and the bending angle of the bending part can be adjusted by moving at least a pair of bending operating wires inserted through the insertion part in conjunction with each other. In the related art, in a case where an endoscope is inserted into the body of a subject, a surgeon, such as a doctor, performs the insertion, for example, while manually operating an operating knob or the like provided in an operating part and adjusting the bending angle of the bending part.

Additionally, an attempt has been made to motor-operate the angle adjustment of the bending part of the endoscope, using a bending operating mechanism driven by, for example, an actuator or the like.

For example, JP2018-114231A discloses an endoscope system in which the bending angle of a bending part is adjusted by fixing a holder provided with a plurality of actuators to an operating part of an endoscope and rotationally operating a manually operating dial provided on the operating part by the actuators.

Additionally, JP2014-223293A discloses an introduction device in which the bending angle of a bending part is adjusted by attachably and detachably connecting a motor to a pulley interlocked with a manually operating knob via a transmission mechanism, such as a gear and pulling or loosening a bending operating wire by the motor via the pulley.

SUMMARY OF THE INVENTION

Meanwhile, endoscopic procedures often require experienced skills, including the delicate sensation of a surgeon. The motorization of the related-art bending operation described in JP2018-114231A and JP2014-223293A is considered as one of techniques for supporting such endoscopic procedures. For example, by using the actuator to motorize the bending operation, the surgeon can release his/her hand from the operating knob and proceed with other work.

However, the motorization of the related-art bending operation is to drive the manually operating knob or dial simply with the actuator. In other words, by motorizing the operation of rotating the manually operating knob or dial, the related-art operation of moving the pair of bending operating wires forward and backward is merely motorized. For this reason, as a technique for supporting an endoscopic procedure that requires experienced skills, it has been required to realize the operation of the bending part with a higher degree of freedom.

The present disclosure has been made. In view of the above-described facts, and an object thereof is to provide an endoscope capable of operating a bending part with a higher degree of freedom while enabling a related-art operation of moving a pair of bending operating wires forward and backward.

An endoscope according to a first aspect of the present disclosure comprises an insertion part having a bendable bending part; an operating part continuously provided on a proximal end side of the insertion part; a pair of bending operating wires inserted into the insertion part and fixed to a distal end side of the insertion part; a first bending operating mechanism that operates the bending part by moving the pair of bending operating wires forward and backward in conjunction with each other; and a second bending operating mechanism that operates the bending part by independently moving the pair of bending operating wires forward and backward.

According to the above configuration, the first bending operating mechanism, which moves the pair of bending operating wires forward and backward in conjunction with each other, and the second bending operating mechanism, which independently moves the pair of bending operating wires forward and backward, are provided. For this reason, it is possible to operate the bending part with a higher degree of freedom while enabling the related-art operation of moving the pair of bending operating wires forward and backward in conjunction with each other. In addition, in the present disclosure, "Independently moving forward and backward" refers to the pair of bending operating wires moving forward and backward separately from each other without being interlocked.

An endoscope according to a second aspect of the present disclosure is the endoscope according to the first aspect, further comprising a bending operating member that inputs a driving force to at least one of the first bending operating mechanism or the second bending operating mechanism by a manual operation.

According to the above configuration, at least one of the first bending operating mechanism or the second bending operating mechanism can be manually operated by the bending operating member.

An endoscope according to a third aspect of the present disclosure is the endoscope according to the second aspect, further comprising a connection interface to which an external mechanism, which inputs a driving force to the other of the first bending operating mechanism and the second bending operating mechanism, is attachably and detachably connected.

According to the above configuration, a driving force can be supplied to the other of the first bending operating mechanism and the second bending operating mechanism by the external mechanism. Here, since the external mechanism is attachably and detachably connected to the connection interface, the external mechanism can be attached and detached as necessary, and appropriate usage is possible depending on procedures.

An endoscope according to a fourth aspect of the present disclosure is the endoscope according to the third aspect in which the bending operating member is capable of inputting a driving force to one of the first bending operating mechanism and the second bending operating mechanism regardless of whether or not the external mechanism is connected to the connection interface.

According to the above configuration, one of the first bending operating mechanism and the second bending operating mechanism can be manually operated in a state where the external mechanism is connected to the connection interface.

An endoscope according to a fifth aspect of the present disclosure is the endoscope according to the third aspect or the fourth aspect in which the external mechanism is an actuator.

According to the above configuration, the other of the first bending operating mechanism and the second bending operating mechanism can be motor-operated by the actuator. Therefore, it is possible to perform other work with a fee hand, and it is possible to perform a more advanced and highly accurate endoscopic procedure.

An endoscope according to a sixth aspect of the present disclosure is the endoscope according to the fifth aspect in which the bending operating member inputs the driving force to the first bending operating mechanism, and the actuator inputs the driving force to the second bending operating mechanism.

According to the above configuration, similarly to the related-art one in which the bending operating wires are moved forward and backward in conjunction with each other, the operation of independently moving the bending operating wire forward and backward while allowing the manual operation can be motorized. For this reason, the manual operation and the motor operation of the bending operating wires can be used together while maintaining the operability of the related-art manual operation.

An endoscope according to a seventh aspect of the present disclosure is the endoscope according to any one of the second aspect to the sixth aspect in which the first bending operating mechanism includes a rotating member that is provided within the operating part and rotates with rotation of the bending operating member, and in a case where the rotating member rotates, one of the pair of bending operating wires is pulled to the proximal end side, and the other is fed to the distal end side.

According to the above configuration, since the first bending operating mechanism has the same configuration as the bending operating mechanism of the related-art endoscope, the related-art endoscope can be used.

An endoscope according to an eighth aspect of the present disclosure is the endoscope according to any one of the first aspect to the seventh aspect in which a first engaging member is provided on each of the pair of bending operating wires on the proximal end side, and the second bending operating mechanism has a pair of second engaging members respectively engaged with the pair of first engaging members and a pair of pulling members that respectively and independently pulls the pair of second engaging members to the proximal end side.

According to the above configuration, the pair of bending operating wires can be independently moved forward and backward by pulling the pair of first engaging members via the pair of second engaging members by the pair of pulling members.

An endoscope according to a ninth aspect of the present disclosure is the endoscope according to the eighth aspect in which the first engaging members independently move away from the second engaging members in a case where the first engaging members move to the proximal end side, and the first engaging members and the second engaging members move together in an engaged state in a case where the first engaging members move to the distal end side.

According to the above configuration, the first engaging members independently move away from the second engaging members in a case where the first engaging members move to the proximal end side. Therefore, the bending operating wires can be operated independently from the second bending operating mechanism by the first bending operating mechanism. On the other hand, the first engaging members and the second engaging members move together in an engaged state in a case where the first engaging members move to the distal end side. Therefore, after the movement, the bending operating wires can be pulled in by the second bending operating mechanism.

An endoscope according to a tenth aspect of the present disclosure is the endoscope according to the ninth aspect in which the first engaging members and the second engaging members move together in an engaged state in a case where the second engaging members move to the proximal end side.

According to the above configuration, the first engaging members and the second engaging members move together in an engaged state in a case where the second engaging members move to the proximal end side. Therefore, the bending operating wires can be pulled via the first engaging members by moving the second engaging members to the proximal end side by the second bending operating mechanism.

An endoscope according to an eleventh aspect of the present disclosure is the endoscope according to the tenth aspect, further comprising a rail member that holds the first engaging members and the second engaging members so as to be movable relative to each other on different axes in a forward and backward direction of the pair of bending operating wires.

According to the above configuration, the first engaging members and the second engaging members can be moved separately by holding the first engaging members and the second engaging members so as to be movable relative to each other on different axes by the rail member.

An endoscope according to a twelfth aspect of the present disclosure is the endoscope according to any one of the eighth aspect to the eleventh aspect, further comprising a stopper that regulates a bending angle of the bending part by abutting against the first engaging members to restrict the movement of the first engaging members.

According to the above configuration, the maximum bending angle of the bending part of the insertion part can be defined by restricting the movement of the first engaging members by the stopper.

An endoscope according to a thirteenth aspect of the present disclosure is the endoscope according to any one of the first aspect to the twelfth aspect in which the pair of bending operating wires are provided in two sets, and the first bending operating mechanism and the second bending operating mechanism are also provided in two sets.

According to the above-described configuration, the endoscope can be operated with two degrees of freedom, up and down and right and left by providing the first bending operating mechanism and the second bending operating mechanism provided in two sets by the pair of first bending operating wires provided in two sets.

According to the present disclosure, it is possible to operate the bending part with a higher degree of freedom while enabling the related-art operation of moving the pair of bending operating wires forward and backward in conjunction with each other.

DESCRIPTION OF THE PREFERRED EMBODIMENTS

Hereinafter, an endoscope according to an example of an embodiment of the present disclosure will be described with reference to the drawings. In addition, in the drawings, arrow X indicates an axial direction of an insertion part of the endoscope or a forward and backward direction of bending operating wires.

Entire Configuration of Endoscope

An endoscope 10 according to the present embodiment is, for example, a medical endoscope that is inserted into a lumen in order to perform treatment or examination of the body of a subject (specifically, the digestive tracts, such as the stomach and the large intestine), and performs treatment, such as collection of biological tissue of an imaging or examination target region within the lumen.

Figure 1:
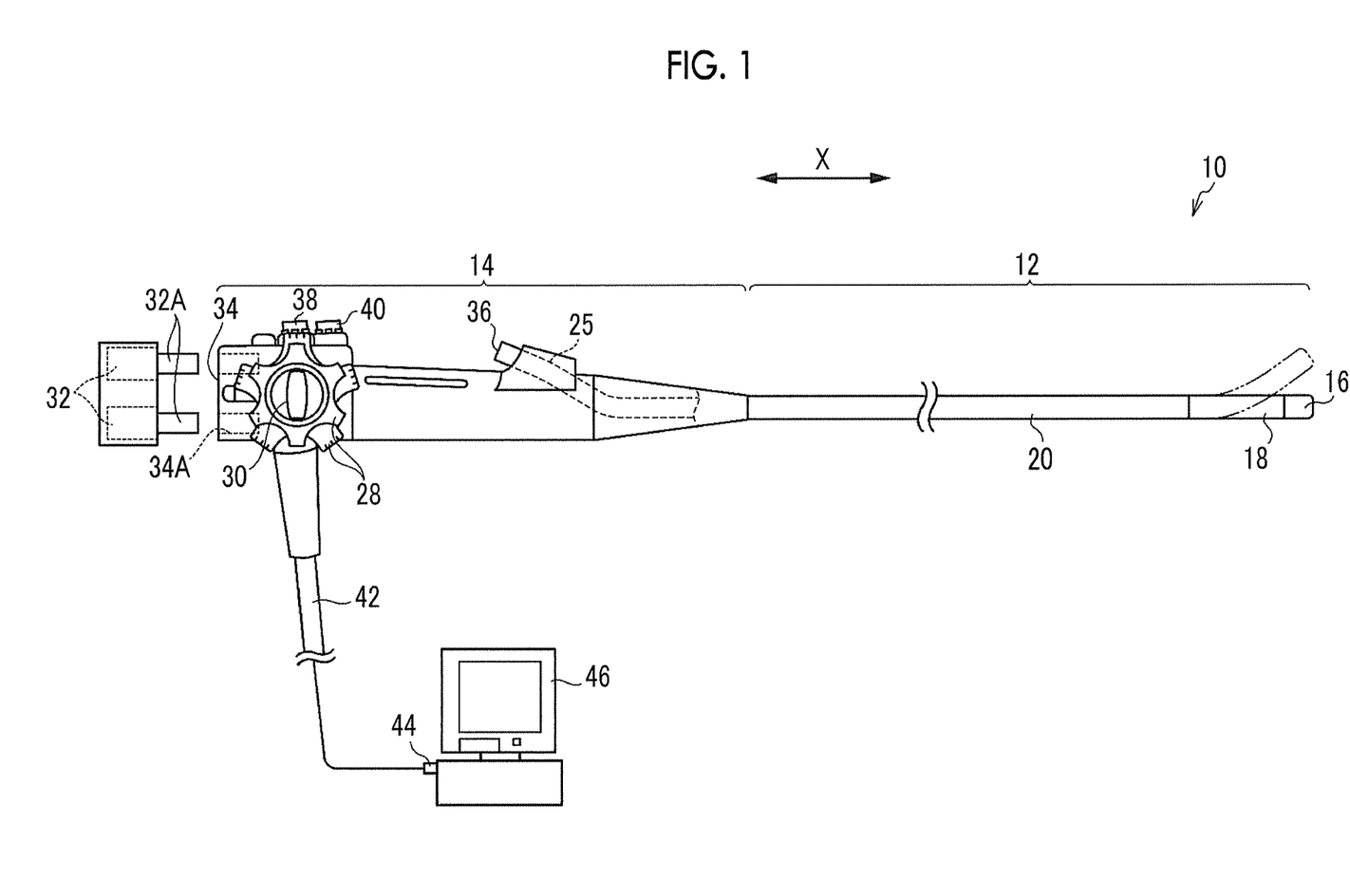
FIG. 1 is an overall schematic view illustrating an endoscope according to an example of an embodiment.

As illustrated in FIG. 1, the endoscope 10 has an insertion part 12 and an operating part 14 provided continuously with the insertion part 12. In addition, hereinafter, a side where the insertion part 12 of the endoscope 10 is provided (a right side in FIG. 1) will be referred to as a "distal end side", and a side where the operating part 14 of the endoscope 10 is provided (a left side in FIG. 1) is referred to as a "proximal end side".

Configuration of Insertion Part

The insertion part 12 is an elongated region to be inserted into the body, and has a hard distal end part 16 provided on the distal end side (that is, an end side opposite to the operating part 14), a bendable bending part 18 connected to the distal end part 16, and a flexible part 20 connected to the bending part 18.

An imaging unit (not illustrated) formed by integrally unitizing a charge coupled device (CCD) sensor, a complementary metal oxide semiconductor (CMOS) sensor, an imaging lens, and the like are incorporated in the distal end part 16. Additionally, the distal end part 16 is also provided with an illumination lens (not illustrated) for irradiating an observation region with illumination light, a forceps outlet (not illustrated) for inserting forceps for collecting biological tissue, a nozzle (not illustrated) for supplying air and water, and the like.

Figure 2:
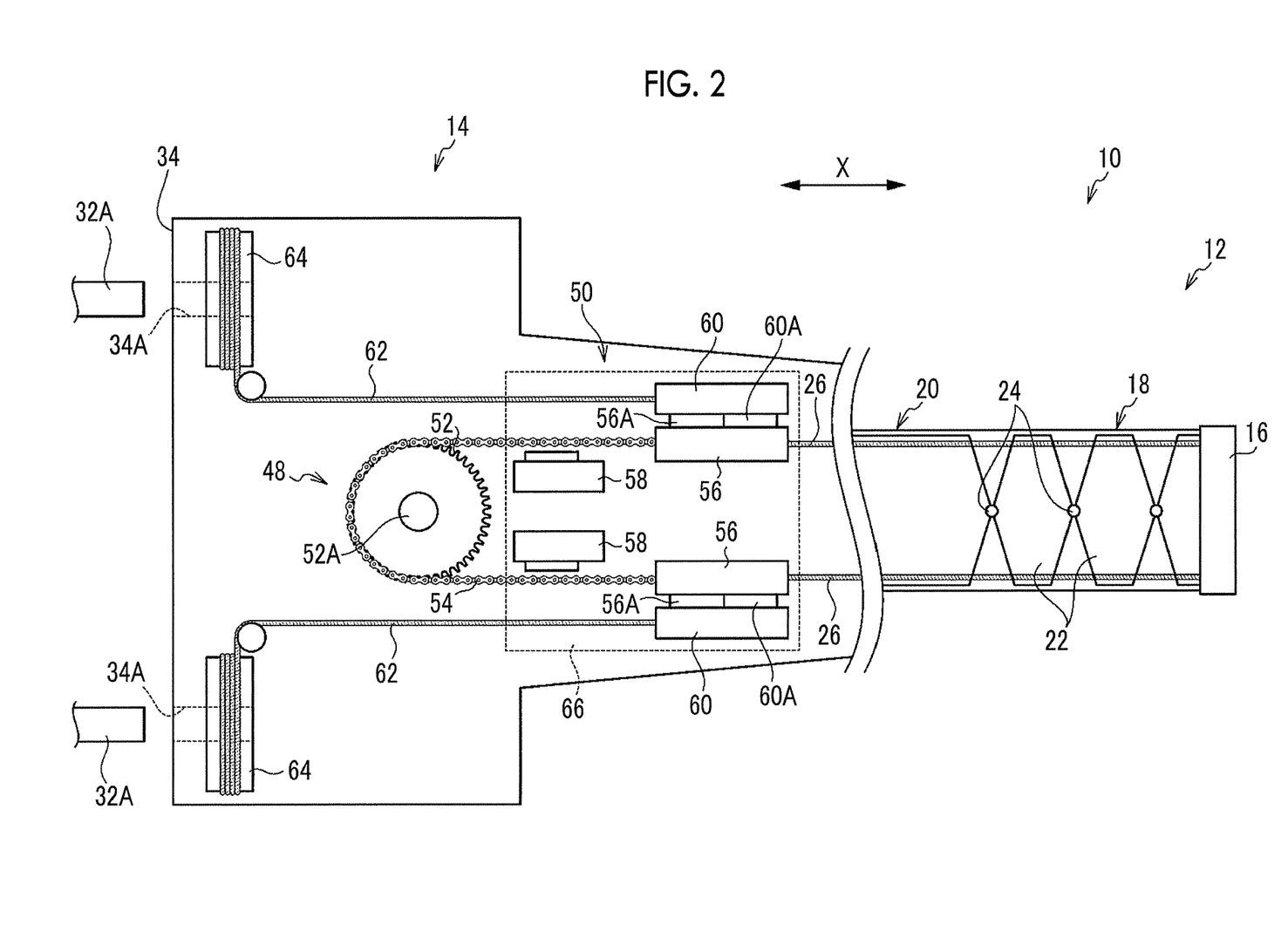
FIG. 2 is a cross-sectional view illustrating an internal configuration of an insertion part and an operating part of the endoscope illustrated in FIG. 1.

The bending part 18 is, for example, a region that bends in four directions, up and down and left and right, in order to insert the distal end part 16 into the body and direct the distal end part toward an observation region. As illustrated in FIG. 2, as an example, the bending part 18 includes a plurality of substantially cylindrical bending pieces 22 and a plurality of pins 24 that couple the bending pieces 22 to each other, and the bending pieces 22 adjacent to each other with a pin 24 as an axis are connected to each other so as to be rotationally movable.

The flexible part 20 is a region that connects the distal end part 16 and the bending part 18 and the operating part 14 to each other and is an elongated tube having flexibility. In addition, built-in objects including a forceps channel 25, an air/water supply channel (not illustrated), a signal line (not illustrated), a light guide (not illustrated), and the like are inserted through the flexible part 20 (and the bending part 18).

Additionally, a pair of bending operating wires 26 that bend the bending part 18 upward and downward, and a pair of bending operating wires (not illustrated) that bend the bending part 18 leftward and rightward are respectively inserted through the flexible part 20 and the bending part 18 of the insertion part 12. The two pairs of bending operating wires 26 are respectively disposed in the axial direction of the insertion part 12 and are engaged with the bending pieces 22 by being inserted through guide parts (not illustrated) provided inside the pins 24 of the bending part 18.

Additionally, end parts of the bending operating wires 26 on the distal end side are respectively fixed to the distal end part 16 of the insertion part 12, and end parts of the bending operating wires 26 on the proximal end side are respectively joined to a pair of first sleeves 56 serving as first engaging members to be described below. Accordingly, the bending part 18 is configured to be bent in a pulling direction by selectively pulling the two pairs of bending operating wires 26 via the first sleeves 56. In addition, operating mechanisms for operating the bending operating wires 26 will be described below in detail.

Configuration of Operating Part

The operating part 14 is a region for operating the endoscope 10 and has a pair of operating knobs 28 serving as bending operating members, as illustrated in FIG. 1. Each operating knob 28 can be manually operated, and the bending part 18 can be operated by inputting a driving force to a first bending operating mechanism 48 (refer to FIG. 2) to be described below by manual operation. In addition, the operating knob 28 is provided with a lock 30 for holding the bending part 18 in a bent state.

Additionally, the operating part 14 has a connection interface 34 to which a plurality of actuators 32 serving as examples of an external mechanism are attachably and detachably connected. An actuator 32 is provided for each bending operating wire 26. That is, one actuator 32 is provided for one bending operating wire 26.

In the present embodiment, since a total of four, i.e., two pairs of bending operating wires 26 are provided, a total of four, i.e., two pairs of (only one pair is illustrated) actuators 32, are provided. In addition, the operation of the actuators 32 can be performed by, for example, a pedal operation with a foot or a voice input, and a surgeon can operate without using his/her hand.

Meanwhile, connection interfaces 34 are provided for the actuators 32, respectively, and are formed with two pairs of (only one pair is illustrated) insertion holes 34A into which drive shafts 32A of the actuators 32 are respectively inserted. Accordingly, the bending part 18 can be operated by inputting the driving force of each actuator 32 to a second bending operating mechanism 50 (refer to FIG. 2) to be described below via an insertion hole 34A and a drive shaft 32A.

Additionally, the operating part 14 is provided with a forceps insertion port 36 for communicating with the forceps outlet (not illustrated) of the distal end part 16 of the insertion part 12 and the forceps channel 25 of the flexible part 20 and for inserting a treatment tool, such as the forceps. Moreover, a suction button 38 for performing suction through the forceps channel 25 from the forceps outlet of the distal end part 16, an air/water supply button 40 for supplying air and water through an air/water supply channel (not illustrated) of the flexible part 20 from the nozzle (not illustrated) provided at the distal end part 16, and the like are disposed.

In addition, the operating part 14 of the endoscope 10 is provided with various switches (not illustrated) for observing or capturing an image with the imaging unit, such as a zoom switch, a still image capturing switch, and a freeze switch.

Additionally, a universal cord 42 is connected to the operating part 14. The water/air supply channel, a suction channel, the light guide, the signal line, and the like (not illustrated) are inserted through the universal cord 42, and the universal cord 42 is connected to an air/water supply device (not illustrated), a light source device (not illustrated), and a processor device 46, and the like via a connector 44.

As illustrated in FIG. 2, the first bending operating mechanism 48, which operates the bending part 18 by moving the pair of bending operating wires 26 forward and backward in conjunction with each other, is provided inside the operating part 14. Additionally, the second bending operating mechanism 50, which operates the bending part 18 by independently moving the pair of bending operating wires 26 forward and backward, is provided inside the operating part 14.

In addition, in the present embodiment, one set of the first bending operating mechanism 48 and the second bending operating mechanism 50 is provided for each of the two pairs of bending operating wires 26. That is, the first bending operating mechanism 48 and the second bending operating mechanism 50, which operate the pair of bending operating wires 26 that bend the bending part 18 upward and downward, and a first bending operating mechanism and a second bending operating mechanism (not illustrated), which operate a pair of bending operating wires (not illustrated) that bend the bending part 18 leftward and rightward, are provided inside the operating part 14.

However, the configuration of the two pairs of bending operating wires 26 and the configuration of the two sets of the first bending operating mechanisms 48 and the second bending operating mechanisms 50 are the same configurations, respectively. For this reason, only one set is illustrated in FIG. 2, and hereinafter, a pair of the bending operating wires 26, which bends the bending part 18 upward and downward, and a set of the first bending operating mechanism 48 and the second bending operating mechanism 50, which operate the pair of bending operating wires 26, will be described.

Configuration of First Bending Operating Mechanism

The first bending operating mechanism 48 has the same configuration as the related-art operating mechanism. Specifically, the first bending operating mechanism 48 has a sprocket 52 serving as a rotating member and a chain 54 wound around the sprocket 52.

Additionally, both end parts of the chain 54 are respectively joined to the pair of first sleeves 56 to which the end parts of the bending operating wires 26 on the proximal end side are joined. In addition, instead of this configuration, a pulley may be used instead of the sprocket 52 as the rotating member, and a wire may be used instead of the chain 54.

The sprocket 52 is supported by one operating knob 28 (refer to FIG. 1) provided in the operating part 14 so as to be rotatable around a rotating shaft 52A. For this reason, by manually operating the operating knob 28 to input a driving force to the sprocket 52 of the first bending operating mechanism 48, the sprocket 52 is rotated with the rotation of the operating knob 28.

Then, via the chain 54 and the first sleeves 56, one of the pair of bending operating wires 26 is pulled to the proximal end side, and the other is fed to the distal end side. That is, the pair of bending operating wires 26 is moved forward and backward by the first bending operating mechanism 48.

In addition, a stopper 58, which restricts the movement of each first sleeve 56 to the proximal end side by abutting against the end part of the first sleeve 56 on the proximal end side, is provided on the proximal end side of the first sleeve 56, that is, between the first sleeve 56 and the sprocket 52. The position of the stopper 58 can be adjusted, and the maximum bending angle of the bending part 18 can be defined by restricting the movement of the first sleeve 56 by the stopper 58.

Configuration of Second Bending Operating Mechanism

The second bending operating mechanism 50 has a pair of second sleeves 60 serving as second engaging members that are respectively engaged with the pair of first sleeves 56, and pulling wires 62 serving as a pair of pulling members.

End parts of the pair of pulling wires 62 on the distal end side are joined to the pair of second sleeves 60, respectively, and end parts of the pair of pulling wires 62 on the proximal end side are wound around the pair of pulleys 64, respectively. The pair of pulleys 64 are, for example, held inside the operating part 14 with the pair of insertion holes 34A formed in the connection interface 34 as rotation centers, and the drive shafts 32A (refer to FIG. 1) of the actuators 32 inserted into the insertion holes 34A can be independently rotated around the drive shafts 32A.

The respective actuators 32 can be independently operated. For this reason, even in a state where the pair of actuators 32 is connected to the connection interface 34, the driving forces of the actuators 32 can be selectively input to the pair of pulleys 64 via the drive shafts 32A. The pulleys 64 to which the driving forces are input rotates, and the pulling wires 62 coupled to the pulleys 64 are wound and pulled to the proximal end side.

Accordingly, each of the pair of second sleeves 60 joined to the pair of pulling wires 62 is independently pulled to the proximal end side. As a result, each of the pair of bending operating wires 26 is independently pulled to the proximal end side via a second sleeve 60 and a first sleeve 56 engaged with the second sleeve 60. That is, each of the pair of bending operating wires 26 is independently forward and backward by the second bending operating mechanism 50.

Configuration of First Sleeve and Second Sleeve

Figure 3:
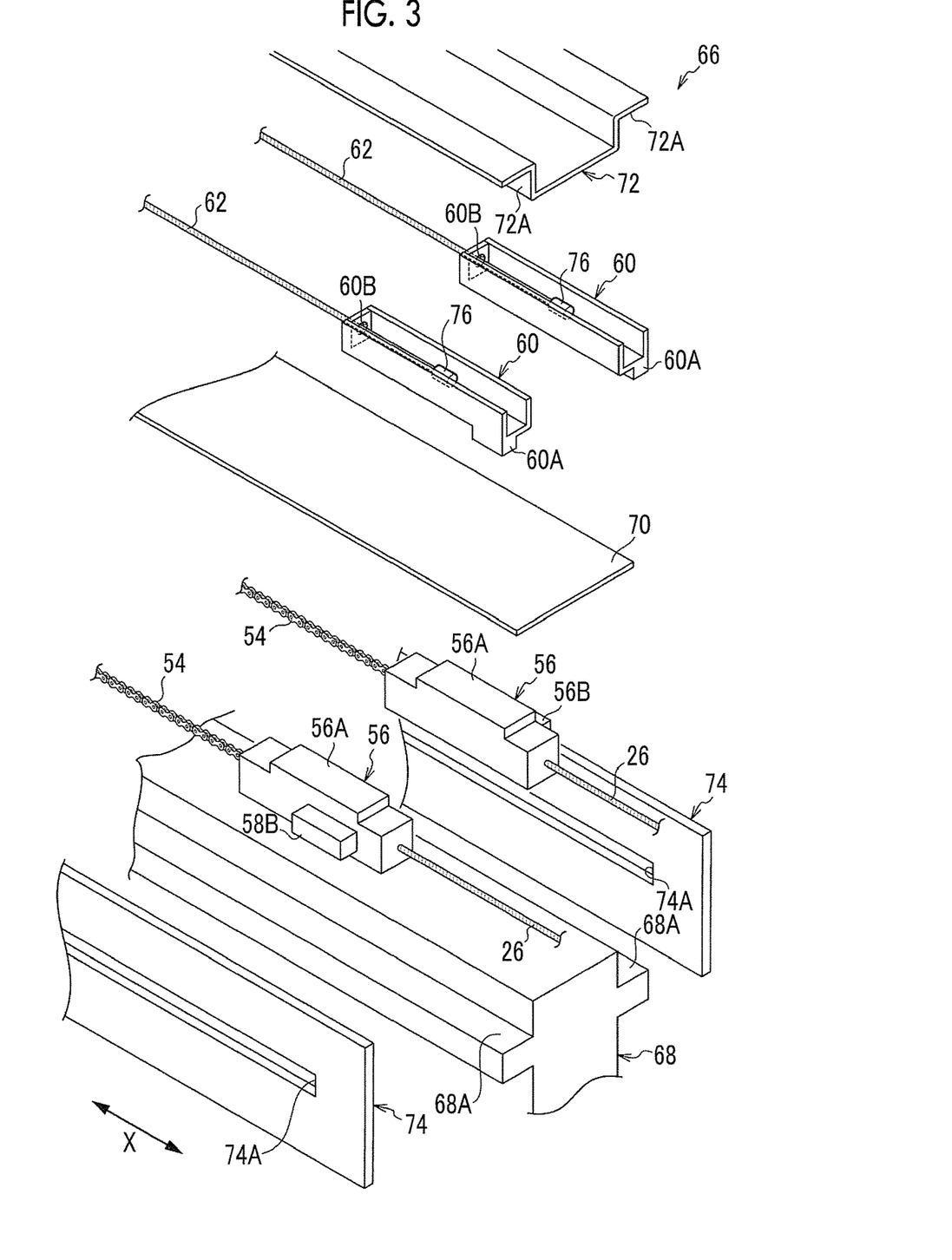
FIG. 3 is an exploded perspective view illustrating the configuration of a first engaging member and a second engaging member of the endoscope illustrated in FIG. 1.
Figure 4:
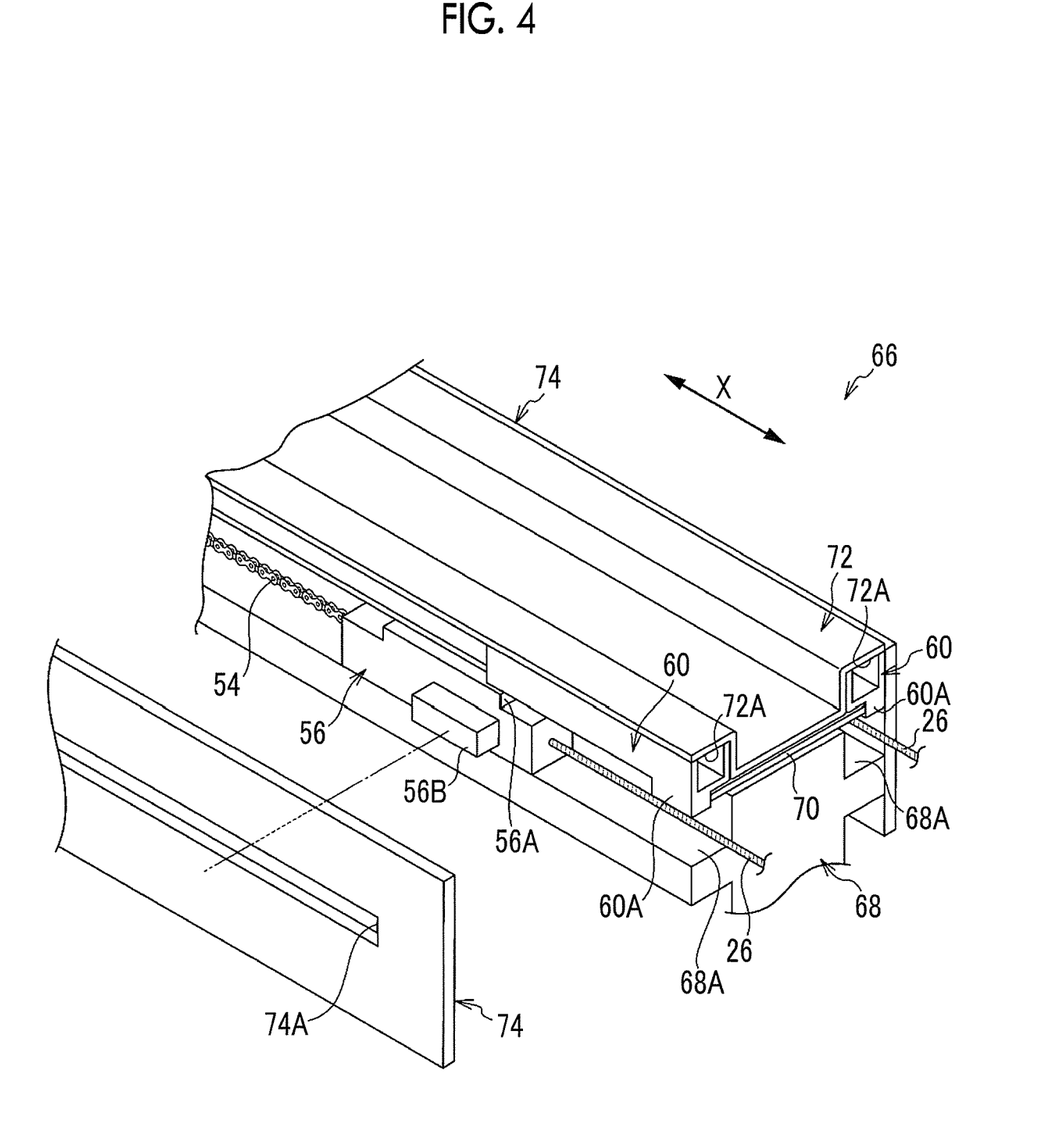
FIG. 4 is a perspective view illustrating the configuration of the first engaging member and the second engaging member of the endoscope illustrated in FIG. 1.

Next, an engagement structure of the first sleeves 56 and the second sleeves 60 will be specifically described. As illustrated in FIGS. 3 and 4, the first sleeves 56 and the second sleeves 60 are held by a rail member 66 so as to be movable relative to each other on different axes in the forward and backward direction of the pair of bending operating wires 26 (that is, the axial direction of the insertion part 12).

The rail member 66 is, for example, a metallic member of which the longitudinal direction extends in the forward and backward direction of the bending operating wires 26. Additionally, the rail member 66 has a base part 68, a plate part 70 placed on the base part 68, a lid part 72 placed on the plate part 70, and a pair of side wall parts 74 disposed on both sides in the width direction orthogonal to the longitudinal direction of the base part 68.

A pair of accommodating recesses 68A, which extends in the forward and backward direction of the bending operating wires 26 and holds the pair of first sleeves 56 so as to be slidable in the forward and backward direction of the bending operating wires 26, is formed on both sides in the width direction on an upper surface of the base part 68.

Similarly, a pair of accommodating recesses 72A, which extends in the forward and backward direction of the bending operating wires 26 and holds the pair of second sleeves 60 so as to be slidable in the forward and backward direction of the bending operating wires 26, is formed on both sides in the width direction on a lower surface of the lid part 72. Additionally, the pair of side wall parts 74 are respectively fondled with slits 74A that extend in the forward and backward direction of the bending operating wires 26.

The first sleeves 56 are rectangular tubular members that extend in the forward and backward direction of the bending operating wires 26, and each has an upper projection 56A that is provided to protrudes from one surface serving as an upper surface and a side projection 56B that is provided to protrude from another surface that faces the side wall part 74. Additionally, end parts of the chain 54 on the distal end side are joined to end surfaces of the first sleeves 56 on the proximal end side, and the end parts of the bending operating wires 26 on the proximal end side are joined to end surfaces of the first sleeves on the distal end side.

The second sleeves 60 are rectangular tubular members that extend in the forward and backward direction of the bending operating wires 26, and each have a lower projection 60A that is provided to protrude from one surface serving as a lower surface. Additionally, a communication hole 60B is formed in an end surface of each second sleeve 60 on the proximal end side, and an end part of each pulling wire 62 on the distal end side is inserted into the second sleeve 60 through the communication hole 60B. In addition, a retaining member 76 having an outer diameter larger than the inner diameter of the communication hole 60B is fixed to the end part of the pulling wire 62 on the distal end side, and the pulling wire 62 is locked to the second sleeve 60 by the retaining member 76.

In a case where the rail member 66 is assembled, first, the pair of first sleeves 56 is respectively accommodated in the pair of accommodating recesses 68A of the base part 68 in such a posture that one surface on which the upper projection 56A is formed is an upper surface. Then, the plate part 70 is installed between the pair of first sleeves 56 on the base part 68, and the second sleeves 60 are installed on both sides of the plate part 70 in such a posture that one surface on which the lower projection 60A is formed is a lower surface.

In this case, each second sleeve 60 is disposed such that the lower projection 60A of the second sleeve 60 is positioned on the distal end side on the same axis in the forward and backward direction of each bending operating wire 26 with respect to the upper projection 56A of each first sleeve 56. That is, in a case where the first sleeve 56 is moved to the distal end side and the second sleeve 60 is moved to the proximal end side, the second sleeve 60 is disposed such that the upper projection 56A of the first sleeve 56 and the lower projection 60A of the second sleeve 60 are engaged with each other.

Thereafter, the lid part 72 is installed on the second sleeves 60 such that each second sleeve 60 is accommodated in each accommodating recess 72A and the side wall parts 74 are respectively fixed to both sides of the base part 68. In this case, the side wall parts 74 are attached such that the side projection 56B of each first sleeve 56 is accommodated within the slit 74A of each side wall part 74. The slit 74A of the side wall part 74 functions as a guide part for moving the side projection 56B of each first sleeve 56 in the forward and backward direction of each bending operating wire 26.

Method of Operating Bending Part

Next, a method of operating the bending part 18 by the first bending operating mechanism 48 and the second bending operating mechanism 50 will be described.

Figure 5:
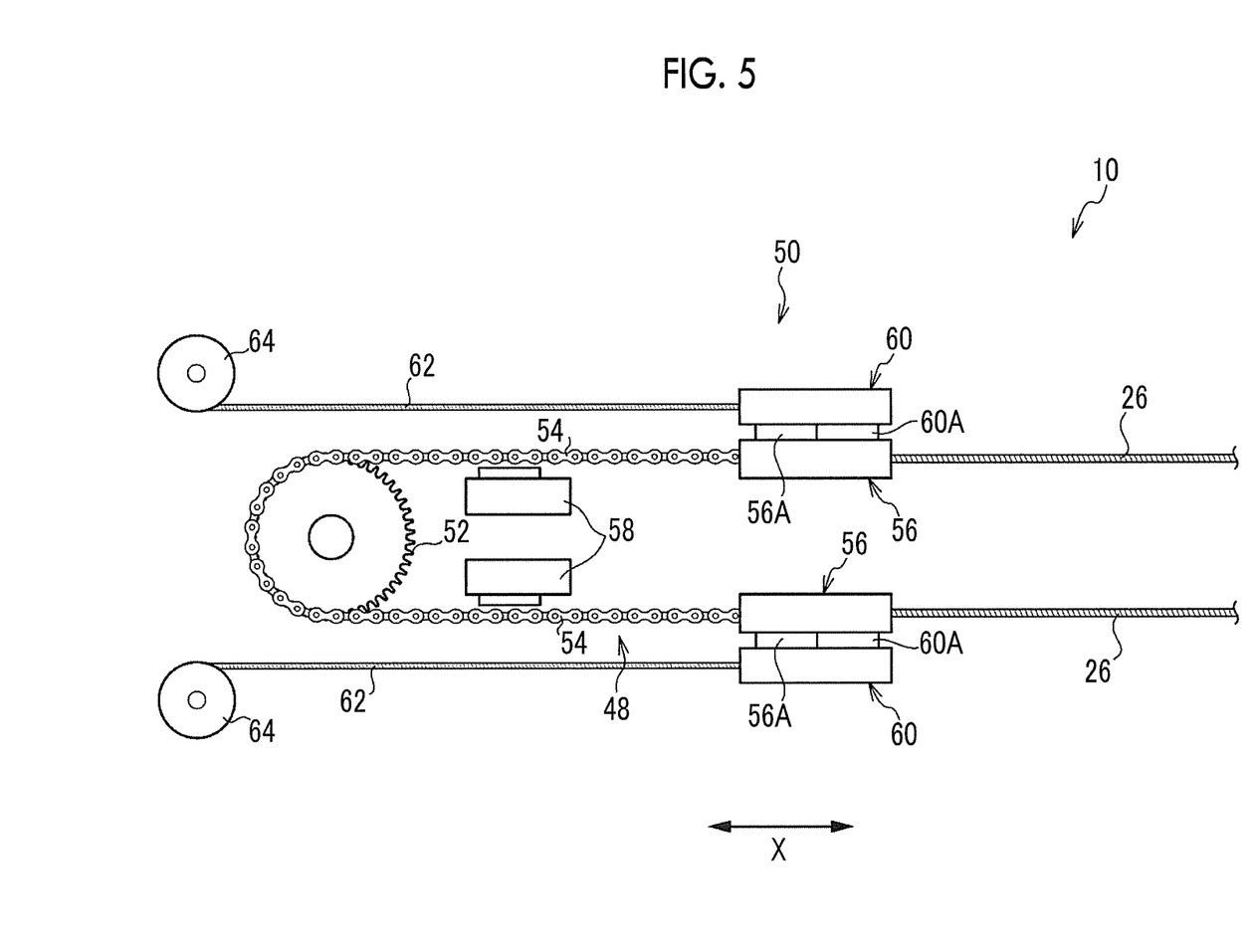
FIG. 5 is an illustrative view schematically illustrating a state before the operation of the first engaging member and the second engaging member of the endoscope illustrated in FIG. 1.

First, an initial state, that is, a state before the bending operating wires 26 is operated will be described. As illustrated in FIG. 5, in the initial state, the first sleeves 56 and the second sleeves 60 are held by the rail member 66 (refer to FIG. 4 and the like) in a state where the upper projection 56A and the lower projection 60A are engaged with each other.

In the initial state, no driving force is input to the first bending operating mechanism 48 and the second bending operating mechanism 50. Therefore, the first sleeves 56 and the second sleeves 60 do not move, and the bending part 18 illustrated in FIG. 2 is brought into a non-bent state (straight state). In addition, in the initial state, the upper projection 56A of each first sleeve 56 and the lower projection 60A of each second sleeve 60 may not be engaged with each other, and a gap may be left in the forward and backward direction of each bending operating wire 26 between the upper projection 56A and the lower projection 60A.

Figure 6:
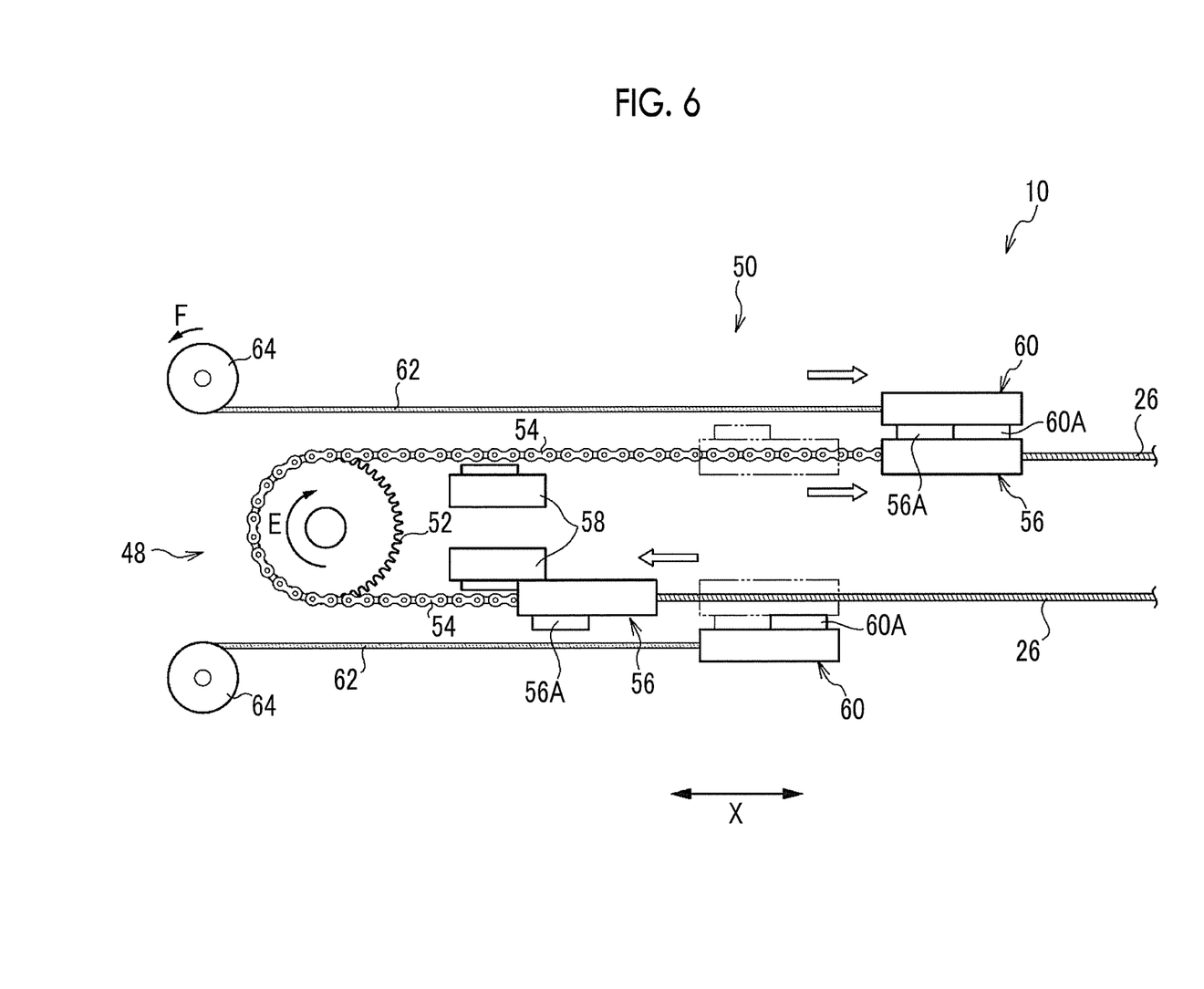
FIG. 6 is an illustrative view schematically illustrating a state during manual operation of the first engaging member and the second engaging member of the endoscope illustrated in FIG. 1.

Next, a case of manual operation, that is, a case where a driving force is input to the first bending operating mechanism 48 by the operating knob 28 (refer to FIG. 1) will be described. As illustrated in FIG. 6, for example, in a case where the sprocket 52 is rotated clockwise (that is, in the direction of arrow E) by the operating knob 28, the lower first sleeve 56 and the lower bending operating wire 26 are pulled by the chain 54 and moved to the proximal end side. On the other hand, the upper first sleeve 56 and the upper bending operating wire 26 are fed and moved to the distal end side, and the bending part 18 illustrated in FIG. 2 is bent downward.

In this case, the lower projection 60A of each second sleeve 60 is engaged with the distal end side of the upper projection 56A of each first sleeve 56. Therefore, during the movement of the upper first sleeve 56 to the distal end side, the upper first sleeve 56 and the upper second sleeve 60 move together in an engaged state. On the other hand, during the movement of the lower first sleeve 56 to the proximal end side, the lower first sleeve 56 independently moves away from the lower second sleeve 60. That is, only the lower first sleeve 56 moves to the proximal end side, and the lower second sleeve 60 does not move.

Additionally, in a case where the actuator 32 (refer to FIG. 1) is not driven, the drive shaft 32A is made rotatable by an external force. For this reason, even in a state where the drive shaft 32A of the actuator 32 is inserted into the insertion hole 34A of the connection interface 34 illustrated in FIG. 2, the drive shaft 32A rotates together with the pulley 64 in a case where an external force is applied.

In a case where each first sleeves 56 is moved to the distal end side by the manual operation of the operating knob 28 (refer to FIG. 1), the first sleeve 56 is engaged with each second sleeve 60, and a force for moving the second sleeve 60 to the distal end side acts on the second sleeve 60. In this case, a rotational force also acts on the pulley 64 through the second sleeve 60 and the pulling wire 62, and the pulley 64 rotates in the direction of arrow F according to the force. For this reason, even in a case where the actuator 32 is not driven, the pulley 64 can be rotated to feed the pulling wire 62, and the second sleeve 60 can be moved to the distal end side together with the first sleeve 56.

That is, regardless of whether or not the actuator 32 is connected to the connection interface 34, a driving force is input to the first bending operating mechanism 48 by the operating knob 28 illustrated in FIG. 1, and the bending part 18 can be operated to be bent. In addition, instead of a configuration in which the drive shaft 32A of the actuator 32 is made rotatable in a case where the drive shaft is not driven, for example, a clutch (not illustrated) may be provided between the pulley 64 and the insertion hole 34A, and during the manual operation, the drive shaft 32A inserted into the insertion hole 34A and the pulley 64 may be brought into a disconnected state by the clutch.

Figure 7:
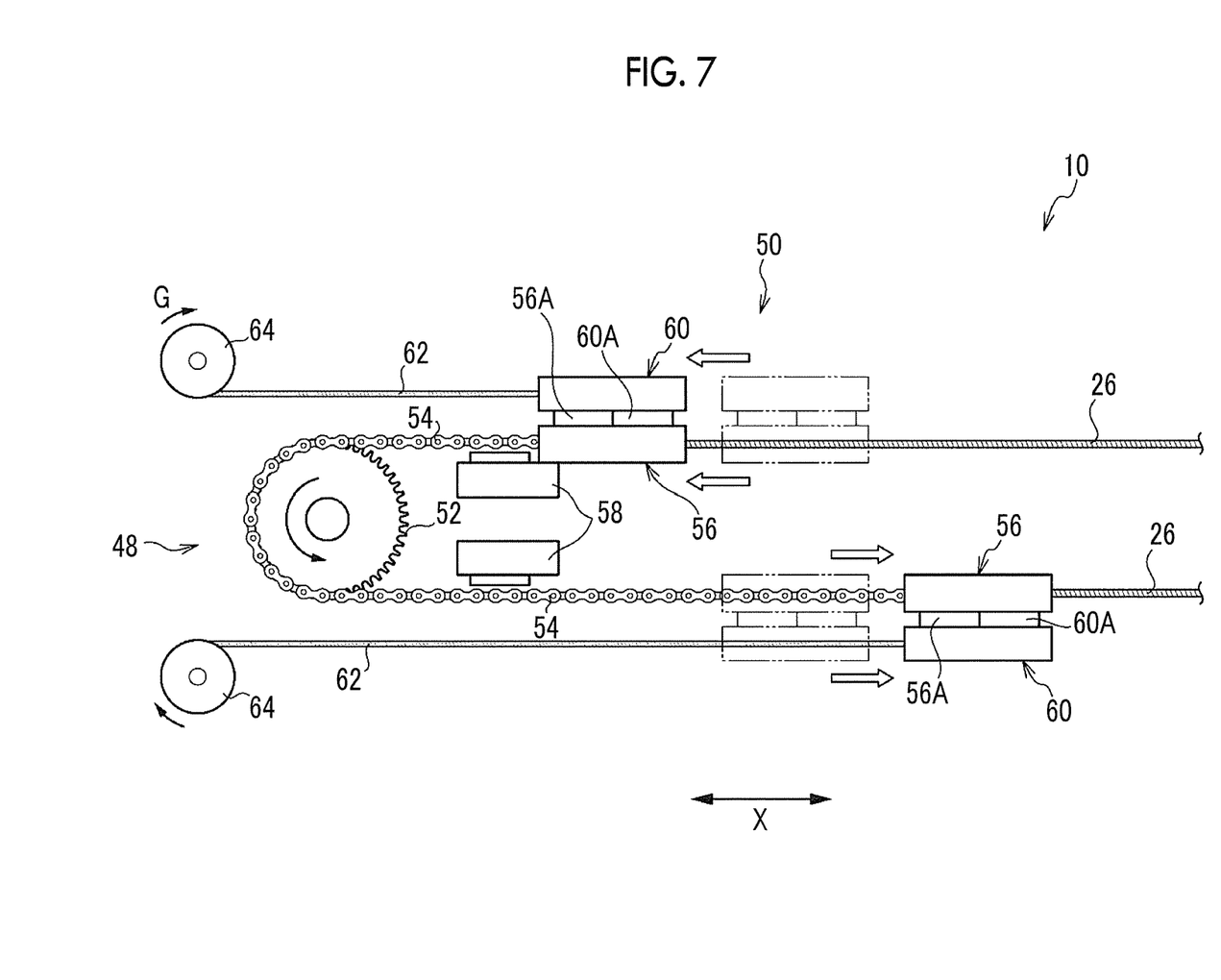
FIG. 7 is an illustrative view schematically illustrating a state during motor operation the first engaging member and the second engaging member of the endoscope illustrated in FIG. 1.

Next, the case of a motor operation, that is, a case where a driving force is input to the second bending operating mechanism 50 by the actuator 32 (refer to FIG. 1) will be described. As illustrated in FIG. 7, for example, in a case where the upper pulley 64 is rotated by the actuator 32 in a direction in which the pulling wire 62 is wound (that is, in the direction of arrow G), the upper second sleeve 60 is pulled by the pulling wire 62 and moved to the proximal end side.

Here, the upper projection 56A of the first sleeve 56 is engaged with the proximal end side of the lower projection 60A of the second sleeve 60. Therefore, in a case where the upper second sleeve 60 moves to the proximal end side, the upper first sleeve 56 and the upper second sleeve 60 move together in an engaged state. That is, the upper first sleeve 56 and the upper bending operating wire 26 move to the proximal end side together with the upper second sleeve 60.

Additionally, as the upper bending operating wire 26 is pulled to the proximal end side, the lower bending operating wire 26 and the lower first sleeve 56 are fed and moved to the distal end side, and the bending part 18 illustrated in FIG. 1 is bent upward. In addition, in a case where the lower first sleeve 56 moves to the distal end side, the lower second sleeve 60, which is engaged with the lower first sleeve 56, also moves to the distal end side together with the lower first sleeve 56.

Figure 8:
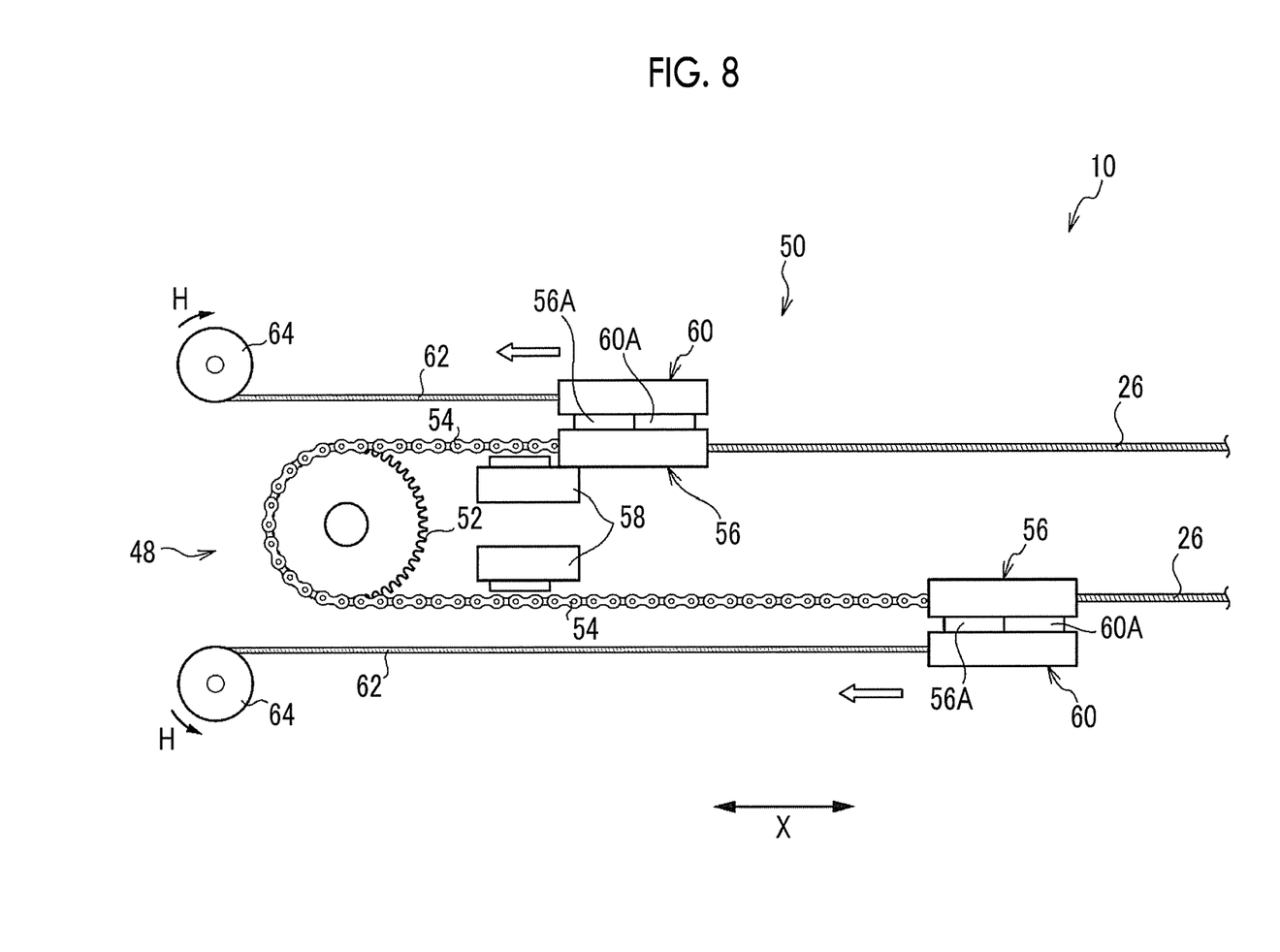
FIG. 8 is an illustrative view schematically illustrating a variation of the motor operation of the first engaging member and the second engaging member of the endoscope illustrated in FIG. 1.

Additionally, in the case of the motor operation, the upper bending operating wire 26 and the lower bending operating wire 26 can be independently moved forward and backward. For this reason, for example, as illustrated in FIG. 8, in a state where the bending part 18 illustrated in FIG. 1 is bent upward, the pair of pulleys 64 are rotated in the direction of arrow H by the actuator 32 (refer to FIG. 1). Accordingly, both the upper pulling wire 62 and the lower pulling wire 62 can be simultaneously wound up.

Accordingly, it is possible to apply a tension to the bending operating wires 26 by pulling both the upper bending operating wire 26 and the lower bending operating wire 26 via the second sleeves 60 and the first sleeves 56. Additionally, by applying the tension to the bending operating wires 26, the bending part 18 can be held at a desired bending angle in a state where the tension is applied to the bending part 18.

Functions and Effects

According to the endoscope 10 of the present embodiment, the first bending operating mechanism 48, which moves the pair of bending operating wires 26 forward and backward in conjunction with each other, and the second bending operating mechanism 50, which independently moves the pair of bending operating wires 26 forward and backward, are provided. For this reason, it is possible to operate the bending part 18 with a higher degree of freedom while enabling the related-art operation of moving the pair of bending operating wires 26 forward and backward in conjunction with each other.

In particular, according to the present embodiment, the first bending operating mechanism 48 is operated by the operating knob 28, and the second bending operating mechanism 50 is operated by the actuator 32. Additionally, the first bending operating mechanism 48 has the sprocket 52 that rotates with the rotation of the operating knob 28, thereby pulling one of the pair of bending operating wires 26 to the proximal end side and feeding the other to the distal end side.

That is, since the first bending operating mechanism 48 has the same configuration as the bending operating mechanism of the related-art endoscope, the mechanism incorporated in the related-art endoscope can be used. Additionally, by using a mechanism similar to the related-art one, the operability of the related-art manual operation of moving the bending operating wires 26 forward and backward can be maintained. In addition, since the manual operation and the motor operation of the bending operating wires 26 can be used together by motorizing the operation of independently moving the bending operating wires 26 forward and backward, it is possible to perform other work with a free hand.

Moreover, as described above, it is possible to perform a more advanced and highly accurate endoscopic procedure that has not been possible in the past, such as holding the bending part 18 in a state where a tension is applied. Specifically, for example, depending on observation regions, there a case where it is desired to increase the bending angle of the bending part 18 and hold the bending part 18 such that the state does not change carelessly. The operation of pulling both of the pair of bending operating wires 26 is effective in such a case.

Additionally, in the related-art endoscope, in a case where a pair of bending operating wires are moved forward and backward in conjunction with each other, the other bending operating wires are fed by pulling one of the bending operating wires. However, in this case, deflection slightly occurs in the other fed bending operating wire. For this reason, in a case where the other bending operating wire is pulled, the other bending operating wire is first pulled by the deflection amount thereof and then the bending part is bent. That is, in the related-art endoscope, the bending (that is, output) of the bending part may be slightly delayed with respect to the operation of the operating knob (that is, the input of a driving force), and the directivity of the operation may be impaired.

Here, according to the present embodiment, as described above, by pulling both the pair of bending operating wires 26 by the actuator 32, the bending operating wires 26 can be held in a state where a tension is applied, and the deflection of the bending operating wires 26 can be eliminated. In this way, by operating the bending operating wires 26 with the operating knob 28 or the actuator 32 in a state in which the deflection of the bending operating wires 26 is eliminated, it is possible to prevent the directivity of the operation from being impaired compared to the related-art case, and the accuracy of operation of the bending part 18 can be increased.

Additionally, according to the endoscope 10 of the present embodiment, the actuator 32 is attachably and detachably connected to the connection interface 34 provided in the operating part 14. For this reason, by attaching and detaching the actuator 32 as necessary, appropriate usage is possible depending on procedures. Additionally, since the actuator 32 can be detached where not in use, it is possible to suppress the operability from being impaired due to an increase in the size of the operating part 14 of the endoscope 10 in a case where the actuator 32 is not used.

Moreover, regardless of whether or not the actuator 32 is connected to the connection interface 34, it is possible to input a driving force to the first bending operating mechanism 48 by the operating knob 28. For this reason, it is not necessary to attach and detach the actuator 32 every time the manual operation and the motor operation are switched, and it is possible to easily switch from the motor operation to the manual operation, for example, in an emergency such as a failure of the actuator 32.

Additionally, according to the present embodiment, the second bending operating mechanism 50 has the pair of second sleeves 60 engaged with the first sleeves 56 joined to the bending operating wires 26 and the pair of pulling wires 62 that pulls the pair of second sleeves 60 to the proximal end side independently from each other. Accordingly, the second bending operating mechanism 50 can independently move the pair of bending operating wires 26 forward and backward via the first sleeves 56.

That is, the first bending operating mechanism 48 and the second bending operating mechanism 50 are respectively connected to the bending operating wires 26 via the first sleeves 56. For this reason, compared to a configuration in which a connecting member that connects the first bending operating mechanism 48 and the bending operating wires 26 to each other and a connecting member that connects the second bending operating mechanism 50 and the bending operating wires 26 are provided separately, an increase in the size of the endoscope 10 can be suppressed.

In particular, according to the present embodiment, in a case where each first sleeve 56 moves to the proximal end side, the first sleeve 56 independently moves away from each second sleeve 60. On the other hand, in a case where the first sleeve 56 moves to the distal end side and in a case where the second sleeve 60 moves to the proximal end side, the first sleeve 56 and the second sleeve 60 move together in an engaged state.

In this way, in a case where the first sleeve 56 is moved to the proximal end side, the bending operating wire 26 can be operated independently from the second bending operating mechanism 50 by the first bending operating mechanism 48 by independently moving the first sleeve 56 away from the second sleeve 60.

Additionally, in a case where the second sleeve 60 moves to the proximal end side, the first sleeve 56 moves together with the second sleeve 60 in an engaged state. For this reason, in a case where the second sleeve 60 is moved to the proximal end side by the second bending operating mechanism 50, the bending operating wire 26 can be pulled via the first sleeve 56.

Additionally, according to the present embodiment, the first sleeves 56 and the second sleeves 60 are held by the rail member 66 so as to be movable relative to each other on different axes in the forward and backward direction of the bending operating wires 26. For this reason, the second bending operating mechanism 50 including the second sleeves 60 can be easily added to the first bending operating mechanism 48 having the same configuration as the related-art one.

Additionally, according to the present embodiment, the stopper 58, which abuts against the first sleeve 56, is provided on the proximal end side of the first sleeve 56. For this reason, by restricting the movement of the first sleeve 56 by the stopper 58, the maximum bending angle of the bending part 18 of the insertion part 12 can be defined.

Moreover, the endoscope 10 according to the present embodiment has the two pairs of bending operating wires 26 and the two sets of the first bending operating mechanisms 48 and the second bending operating mechanisms 50. In this way, by operating the pairs of bending operating wires 26 provided in two sets by the first bending operating mechanisms 48 and the second bending operating mechanisms 50 provided in two sets, the four bending operating wires 26 can be controlled, respectively, while the endoscope 10 can be operated with two degrees of freedom, up and down and left and right.

Other Embodiments

Although the example of the embodiment of the present disclosure has been described above, the present disclosure is not limited to the above embodiment at all, and can be carried out in various aspects without departing the spirit of the present disclosure.

Figure 9:
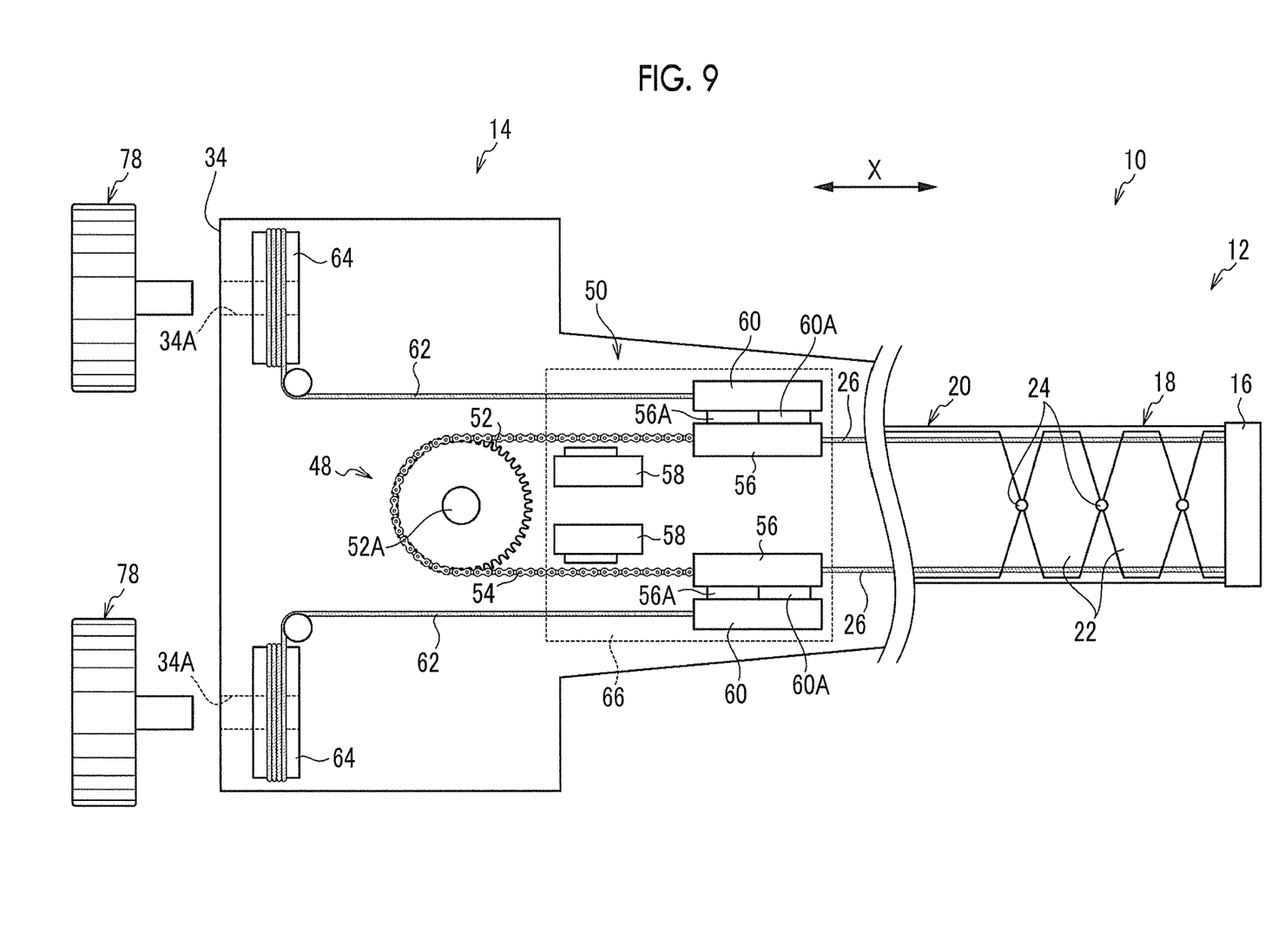
FIG. 9 is a partially cross-sectional view illustrating an endoscope according to a modification example.

For example, in the above embodiment, the first bending operating mechanism 48 is manually operated by the operating knob 28, and the second bending operating mechanism 50 is motor-operated by the actuator 32. However, similarly to the first bending operating mechanism 48, the second bending operating mechanism 50 may be manually operated. In this case, for example, as illustrated in FIG. 9, the second bending operating mechanism 50 can be manually operated by connecting a plurality of operating knobs 78 serving as external mechanisms to the connection interface 34 and manually operating the operating knobs 78.

Additionally, contrary to the above-described embodiment illustrated in FIG. 1, the first bending operating mechanism 48 may be motor-operated by the actuator 32 and the second bending operating mechanism 50 may be manually operated by the operating knob 28. Additionally, a configuration in which an actuator is connected to the operating knob 28 and the operating knob 28 is motor-operated, that is, a configuration in which both the first bending operating mechanism 48 and the second bending operating mechanism 50 are motor-operated may be adopted.

Additionally, in the above embodiment, the operating knob 28 is used as the bending operating member. However, the bending operating member only needs to be configured to be capable of inputting a driving force to at least one of the first bending operating mechanism 48 or the second bending operating mechanism 50 by manual operation t. For example, an operating lever, a joystick, or a screw-type knob may be used.

EXPLANATION OF REFERENCES

10: endoscope
12: insertion part
14: operating part
16: distal end part
18: bending part
20: flexible part 22: bending piece
24: pin
26: bending operating wire
28: operating knob (example of bending operating member)
30: lock
32: actuator (example of external mechanism)
32A: drive shaft
34: connection interface
34A: insertion hole
36: forceps port
38: suction button
40: air/water supply button
42: universal cord
44: connector
46: processor device
48: first bending operating mechanism
50: second bending operating mechanism
52: sprocket (example of rotating member)
52A: rotating shaft
54: chain
56: first sleeve (example of first engaging member)
56A: upper projection
56B: side projection
58: stopper
60: second sleeve (example of second engaging member)
60A: lower projection
60B: communication hole
62: pulling wire (example of pulling member)
64: pulley
66: rail member
68: base part
68A: accommodating recess
70: plate part
72: lid part
72A: accommodating recess
74: side wall part
74A: slit
76: retaining member
78: operating knob (example of external mechanism)

What is claimed is:

1. An endoscope comprising:
an insertion part having a bendable bending part;
an operating part continuously provided on a proximal end side of the insertion part;
a pair of bending operating wires inserted into the insertion part and fixed to a distal end side of the insertion part;
a first bending operating mechanism that operates the bending part by moving the pair of bending operating wires forward and backward in conjunction with each other; and
a second bending operating mechanism that operates the bending part by independently moving the pair of bending operating wires forward and backward,
wherein a first engaging member is provided on each of the pair of bending operating wires on the proximal end side,
wherein the second bending operating mechanism has a pair of second engaging members respectively engaged with the pair of first engaging members and a pair of pulling members that respectively and independently pulls the pair of second engaging members to the proximal end side,
wherein the first engaging members independently move away from the second engaging members in a case where the first engaging members move to the proximal end side,
wherein the first engaging members and the second engaging members move together in an engaged state in a case where the first engaging members move to the distal end side.

2. The endoscope according to claim 1, further comprising:
a bending operating member that inputs a driving force to at least one of the first bending operating mechanism or the second bending operating mechanism by a manual operation.

3. The endoscope according to claim 2, further comprising:
a connection interface to which an external mechanism, which inputs a driving force to the other of the first bending operating mechanism and the second bending operating mechanism, is attachably and detachably connected.

4. The endoscope according to claim 3,
wherein the bending operating member is capable of inputting a driving force to one of the first bending operating mechanism and the second bending operating mechanism regardless of whether or not the external mechanism is connected to the connection interface.

5. The endoscope according to claim 3,
wherein the external mechanism is an actuator.

6. The endoscope according to claim 5,
wherein the bending operating member inputs the driving force to the first bending operating mechanism, and
wherein the actuator inputs the driving force to the second bending operating mechanism.

7. The endoscope according to claim 2,
wherein
the rotating member that is provided within the operating part and rotates with rotation of the bending operating member, and
wherein in a case where the rotating member rotates, one of the pair of bending operating wires is pulled to the proximal end side, and the other is fed to the distal end side.

8. The endoscope according to claim 1,
wherein the first engaging members and the second engaging members move together in an engaged state in a case where the second engaging members move to the proximal end side.

9. The endoscope according to claim 8, further comprising:
a rail member that holds the first engaging members and the second engaging members so as to be movable relative to each other on different axes in a forward and backward direction of the pair of bending operating wires.

10. The endoscope according to claim 1, further comprising:
a stopper that regulates a bending angle of the bending part by abutting against the first engaging members to restrict the movement of the first engaging members.

11. The endoscope according to claim 1,
wherein the pair of bending operating wires are provided in two sets, and
wherein the first bending operating mechanism and the second bending operating mechanism are also provided in two sets.

* * * * *